(12) United States Patent
Schouten

(10) Patent No.: US 9,376,706 B2
(45) Date of Patent: Jun. 28, 2016

(54) PROTEASE DETECTION

(71) Applicant: Mologic Limited, Bedfordshire (GB)

(72) Inventor: James A. Schouten, Beds (GB)

(73) Assignee: Mologic Limited, Bedfordshire (GB)

( * ) Notice: Subject to any disclaimer, the term of this patent is extended or adjusted under 35 U.S.C. 154(b) by 0 days.

(21) Appl. No.: 14/553,182

(22) Filed: Nov. 25, 2014

(65) Prior Publication Data

US 2015/0152471 A1 Jun. 4, 2015

Related U.S. Application Data

(62) Division of application No. 12/742,867, filed as application No. PCT/GB2008/003833 on Nov. 13, 2008, now Pat. No. 8,993,253.

(30) Foreign Application Priority Data

Nov. 13, 2007 (GB) .................................. 0722287.0

(51) Int. Cl.
| | |
|---|---|
| *C12Q 1/37* | (2006.01) |
| *B01L 3/00* | (2006.01) |
| *C07K 5/083* | (2006.01) |
| *C07K 7/06* | (2006.01) |
| *G01N 33/58* | (2006.01) |

(52) U.S. Cl.
CPC .................. *C12Q 1/37* (2013.01); *B01L 3/5055* (2013.01); *C07K 5/0808* (2013.01); *C07K 7/06* (2013.01); *G01N 33/583* (2013.01); *B01L 2300/0809* (2013.01)

(58) Field of Classification Search
None
See application file for complete search history.

(56) References Cited

U.S. PATENT DOCUMENTS

| 4,675,290 A | * | 6/1987 | Matsumoto et al. | ............. | 435/24 |
|---|---|---|---|---|---|
| 4,784,944 A | * | 11/1988 | Kolde | .............................. | 435/13 |

FOREIGN PATENT DOCUMENTS

| GB | 2185025 A | | 7/1987 |
|---|---|---|---|
| WO | WO-2007/096642 A1 | | 8/2007 |
| WO | WO 2007096637 A1 | * | 8/2007 |
| WO | WO 2007096642 A1 | * | 8/2007 |

OTHER PUBLICATIONS

Wang, Shu-Ping, and Hwei-Jun Chen. "Separation and determination of nitrobenzenes by micellar electrokinetic chromatography and high-performance liquid chromatography." Journal of Chromatography A 979.1 (2002): 439-446.*
Cristau, M., et al.; "Synthesis and Biological Evaluation of Bombesin Constrained Analogues," J. Med. Chem., 43(12): 2356-2361 (Jun. 15, 2000).
Cui, Yong-Mei, et al.; "Design and synthesis of chromogenic thiopeptolide substrates as MetAPs active site probes," Bioorganic & Medicinal Chemistry, 12(11): 2853-2861 (Jun. 1, 2004).
Fitzgerald, Michael C., et al.; "A Continuous Fluorometric Assay for the Feline Immunodeficiency Virus Protease," Analytical Biochemistry 254: 226-230 (1997).
Ishida, Hitoshi, et al.; "Artificial Peptides with Unnatural Components Designed for Materializing Protein Function," Biopolymers (Peptide Science) 55: 469-478 (2000).
Knight, C. Graham; "Fluorimetric Assays of Proteolytic Enzymes," Methods in Enzymology, 248: 18-34 (Jan. 1, 1995).
Qian, Y., et al.; "Probing the Hydrophobic Pocket of Farnesyltransferase: Aromatic Substitution of CAAX Peptidomimetics Leads to Highly Potent Inhibitors," Bioorganic & Medicinal Chemistry 7(12): 3011-3024 (Dec. 1999).
Peng, Sheng-Bin, et al.; "Development of an Internally Quenched Fluorescent Substrate and a Continuous Fluorimetric Assay for *Streptococcus pneumoniae* Signal Peptidase I," Analytical Biochemistry 293: 88-95 (2001).
Weerapana, E, et al.; "Peptides to peptidomimetics: towards the design and synthesis of bioavailable inhibitors of oligosaccharyl transferase," Organic and Biomolecular Chemistry, 1(1): 93-99 (Jan. 7, 2003).
International Search Report for PCT/GB2008/003833 mailed on Jun. 24, 2009.
UK Search Report for Application No. GB0722287.0 date of search Mar. 11, 2008.
Rijkers, Dirk, T.S., et al. "Synthesis of peptide *p*-nitroanilides mimicking fibrinogen-and hirudin-binding to thrombin," Int. J. Peptide Protein Res., 48:182-193 (1996).

* cited by examiner

*Primary Examiner* — Robert Yamasaki
(74) *Attorney, Agent, or Firm* — Foley Hoag LLP

(57) ABSTRACT

A polypeptide comprising a chromogenic amino acid. The chromogenic amino acid is flanked by at least one amino acid to the N and C termini thereof. The amine group of the chromogenic amino acid has a pKa of less than 5. The chromogenic amino acid is capable of reacting with a conjugated aldehyde. The polypeptide comprises a target sequence for a target protease which is capable of cleaving the peptide bond comprising the amino group of the chromogenic amino acid.

7 Claims, 10 Drawing Sheets

|  |  |
|---|---|
| Positive result | Negative result |
| Pantone ref: Solid uncoated 1505 U | Pantone ref: Solid uncoated 3945 U |

PROTEASE DETECTION

This application is a divisional application of U.S. Ser. No. 12/742,867 filed Oct. 6, 2010; now U.S. Pat. No. 8,993,253, which is a 371 national stage application of PCT/GB2008/003833, filed Nov. 13, 2008, which claims priority to GB 0722287.0, filed Nov. 13, 2007. The entire contents of each of these applications are hereby incorporated by reference.

The present invention relates to a polypeptide comprising a chromogenic amino acid, a product incorporating such a polypeptide and a method of manufacturing such a polypeptide. The invention also relates to a method of detecting a protease enzyme.

A number of reagents or compounds are known in the art for use in the measurement of proteolysis. These include synthetically modified polypeptide substrates which release an indicator moiety or labile molecule when cleaved proteolytically, such as synthetic polypeptides that have been modified as p-nitroanilides or napthylamines at their C-termini. For example, EP-A-0864864 discloses the detection of protease enzymes using Dnp-Pro-β-cyclohexyl-Ala-Gly-Cys (Mu)-His-Ala-Lys(N-Me-Abz)-NH$_2$ which is a fluorescent based peptide, rather than a chromogenic peptide. Plapinger et al. J. Org. Chem 1965, 30, 1781 report on chromogenic substrates, cleaved by trypsin, that are derivatives of arginine.

After a p-nitroaniline is cleaved from the C-terminus of such a peptide substrate and liberated into the solution, an increase in UV absorbance can be measured. In the case of peptide substrates comprising naphthylamines, the released chromogenic moiety can be trapped by an additional reporter molecule to produce a visible colour change. The synthetic trypsin substrate Na-benzoyl-DL-arginine-β-naphthalamine (BANA) is commonly used in assays for proteolytic activity, for example, to aid the diagnosis of periodontal disease.

The chromogenic protease substrates known in the art, such as BANA, have their respective chromogenic moieties positioned at the C-terminus of the polypeptide (with the exception of Thiopeptolides, see below). The problem with such chromogenic protease substrates is that, with the chromogenic moiety positioned at the C-terminus of the polypeptide, there is limited protease specificity due to the restricted format of the polypeptide lacking flanking amino acids. The chromogenic peptides known in the art also have poor water solubility, and the synthesis of longer polypeptides adds complexity to the synthesis process. This makes formulation of the polypeptides difficult and adds to the cost of increasing manufacture of the polypeptides on a commercial scale.

In addition, the C-terminal chromogen cannot be conjugated to a solid surface in a straightforward manner, which limits the methods that can be employed for visualising a result of proteolysis using these polypeptides in a diagnostic.

Thiopeptolides, as described in Weingarten et al. Biochem, 1985, 24, 6730-6734, have chromogenic moieties internal to the peptide sequence, but do not use an amide bond. The problem with peptide substrates based on Thiopeptolides is that, because they do not comprise the usual amide bond at the site of proteolytic cleavage, they may not offer maximal substrate recognition or turnover.

The present invention seeks to alleviate one or more of the above problems.

According to one aspect of the present invention, there is provided a polypeptide comprising a chromogenic amino acid, wherein the chromogenic amino acid is flanked by at least one amino acid to the N and C termini thereof.

Preferably, the amine group of the chromogenic amino acid has a pKa of less than 5 and the chromogenic amino acid is capable of reacting with a conjugated aldehyde.

Advantageously, the polypeptide comprises a target sequence for a target protease which is capable of cleaving the peptide bond comprising the amino group of the chromogenic amino acid.

There is also provided in accordance with the present invention a polypeptide comprising a chromogenic amino acid, wherein the chromogenic amino acid is flanked by at least one amino acid to the N and C termini thereof, the amine group of the chromogenic amino acid has a pKa of less than 5 and the chromogenic amino acid is capable of reacting with a conjugated aldehyde, and wherein the polypeptide comprises a target sequence for a target protease which is capable of cleaving the peptide bond comprising the amino group of the chromogenic amino acid.

Conveniently, the chromogenic amino acid comprises an aromatic ring moiety directly bonded to the nitrogen atom of the amino group of the chromogenic amino acid.

Preferably, the chromogenic amino acid isosterically matches a natural amino acid.

Conveniently, the target sequence comprises the chromogenic amino acid.

Preferably, the chromogenic amino acid is capable of reacting with the conjugated aldehyde to give a detectable signal, when the target sequence is cleaved.

Advantageously, the conjugated aldehyde is a substituted benzaldehyde or a cinnamaldehyde or a trans,trans phenyl pentadienal.

Preferably, the conjugated aldehyde is DMAC or DMAB.

Conveniently, the aromatic moiety is a phenyl or naphthyl moiety.

Advantageously, the polypeptide is a linear polypeptide.

Preferably, the polypeptide is immobilised on a solid surface at or near the C or N terminus of the polypeptide.

Advantageously, the polypeptide is covalently bound to the solid surface.

Conveniently, the polypeptide further comprises first and second binding moieties at or near the C or N terminus of the polypeptide.

Preferably, the polypeptide is between 2 and 100 amino acids long, more preferably between 3 and 40 amino acids long.

According to another aspect of the present invention, there is provided a method of detection of a protease enzyme in a sample, comprising the steps of:
(i) exposing the sample to a polypeptide according to any one of the preceding claims and allowing the protease to cleave the polypeptide and create a fragment displaying the chromogenic amino acid to the N-terminus of the fragment;
(ii) reacting a conjugated aldehyde with the fragment comprising the chromogenic amino acid to produce a coloured adduct; and
(iii) detecting the coloured adduct, the presence of the coloured adduct being indicative of the presence of the protease enzyme in the sample Conveniently, step (i) comprises the protease enzyme cleaving the peptide bond of the polypeptide comprising the amino group of the chromogenic amino acid.

According to a further aspect of the present invention, there is provided a method of manufacture of the invention comprising the steps of:
i. synthesising an amino acid dimer comprising one chromogenic amino acid; and
ii. incorporating the dimer into the remainder of the polypeptide during synthesis of the polypeptide.

Conveniently, step (ii) comprises coupling the dimer to a nascent oligopeptide.

According to another aspect of the present invention, there is provided a product for detecting a protease enzyme in a sample comprising:

a polypeptide according to the invention; and
a solid support, on which the polypeptide is immobilisable.

Preferably, the product further comprises a conjugated aldehyde.

Advantageously, the solid support comprises first and second hingedly connected sheets, the polypeptide being immobilised on the first sheet and the conjugated aldehyde being located on the second sheet, such that folding the sheets together permits transfer of material from the first sheet to the second sheet.

Conveniently, the product further comprises a membrane interposable between the polypeptide immobilised on the first sheet and the conjugated aldehyde located on the second sheet, the membrane preventing passage of material having a size greater than a threshold size from the first sheet to the second sheet, the polypeptide being cleavable by a protease enzyme to release a fragment comprising the chromogenic amino acid, the fragment being smaller than the threshold size.

Alternatively, the solid support comprises a chromatographic medium.

Advantageously, the chromatographic medium further comprises a fragment binding molecule capable of binding a fragment of the polypeptide comprising the chromogenic amino acid releasable from the polypeptide following cleavage by a protease enzyme, the polypeptide being immobilisable on the chromatographic medium at a marking zone and the fragment binding molecule being immobilised on the chromatographic medium at a visualisation zone.

Conveniently, the polypeptide is cleavable into first and second fragments the first fragment comprising the chromogenic amino acid, and wherein the product further comprises: a detectable label associatable with the second fragment; and first and second capture molecules immobilised in or on the chromatographic medium, the first capture molecule being capable of binding the first fragment and the second capture molecule being capable of binding the second fragment or the detectable label.

Preferably, the label comprises a binding component capable of binding the second fragment.

Advantageously, the chromatographic medium comprises a test strip.

Alternatively, the chromatographic medium comprises a column of porous material.

According to a further aspect of the present invention, there is provided a synthetic polypeptide comprising a plurality of material amino acids and at least one chromogenic amino acid that isosterically matches a natural amino acid.

According to another aspect of the present invention, there is provided the use of a synthetic polypeptide according to the invention for the detection of a protease enzyme in a sample.

Embedding the chromogenic moiety within the peptide sequence reduces the impact of hydrophobicity on synthesis and use. Since the chromogen in the present invention is within the peptide sequence, the C and N terminals of the peptide are free for use with standard coupling chemistries familiar to those skilled in the art.

A "chromogenic amino acid" in this specification means an amino acid molecule (containing an amino group and a carboxylic group) capable of changing colour. More specifically, it can form a coloured adduct measurable between 400 and 900 nm, when it is positioned at the P1' position in a protease cleavage site in a peptide substrate, liberated via proteolysis and subsequently reacted with a second molecule via covalent chemistry.

A "target protease" in this specification is defined as a protease that recognises and cleaves a target region on a chromogenic polypeptide, wherein the target region comprises a chromogenic amino acid at the P1' position of the cleavage site.

"Natural amino acid" means any one of the following amino acids: Alanine, Arginine, Asparagine, Aspartic acid, Cysteine, Glutamine, Glutamic acid, Glycine, Histidine, Isoleucine, Leucine, Lysine, Methionine, Phenylalanine, Proline, Serine, Threonine, Tyrosine, Tryptophan and Valine.

A "flanked" amino acid in this specification is an amino acid that is linked to at least one further amino acid, wherein this linkage occurs via a peptide bond between the amino terminus of one amino acid and the carboxyl group of the other.

An "isosteric match" in this specification is used in association with a natural amino acid and a corresponding chromogenic amino acid. It means that the matched substituted chromogenic amino acid has a similar spacial occupancy to that of the natural amino acid it replaces. A chromogenic amino acid can be considered to be an isosteric match for a natural amino acid if a protease specific for a peptide sequence comprising the natural amino acid will also cleave a polypeptide in which the chromogenic amino acid is substituted for the natural amino acid.

Figure 6:
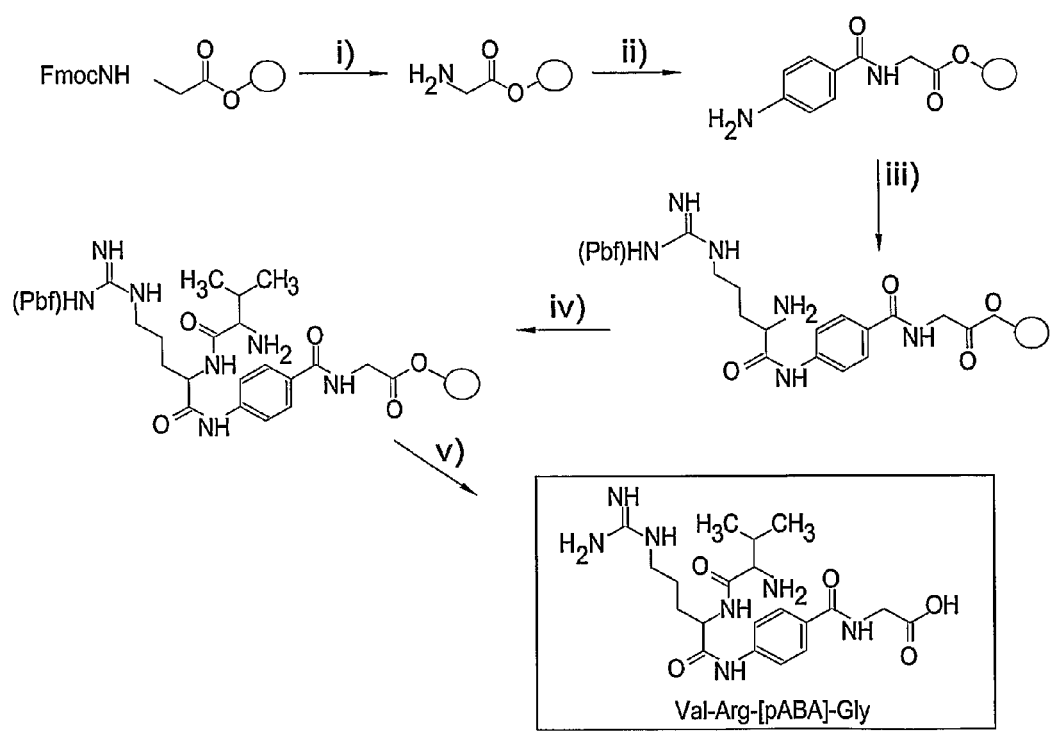

FIG. 6 is a flow chart showing a method of synthesising a polypeptide in accordance with another embodiment of the present invention. The sequence Val-Arg-[p-ABA]-Gly (SEQ ID NO: 2) is used as an example synthesised on solid phase (resin depicted by circle). The key reaction in the synthesis of the molecule is step iii). This reaction is not readily achievable with standard peptide chemistry using an activated ester of the incoming amino acid. However, using the acid chloride of the incoming amino acid substantially improves the reaction chemistry.

Figure 7A:
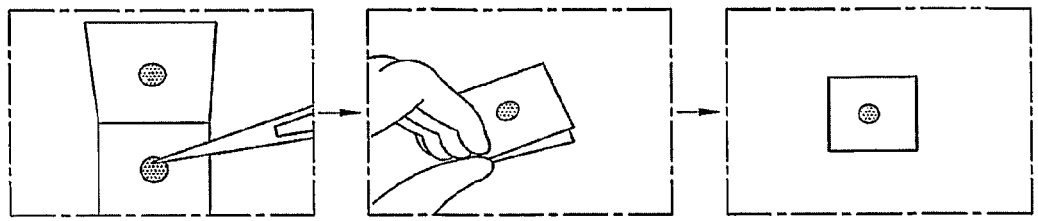
Figure 7B:
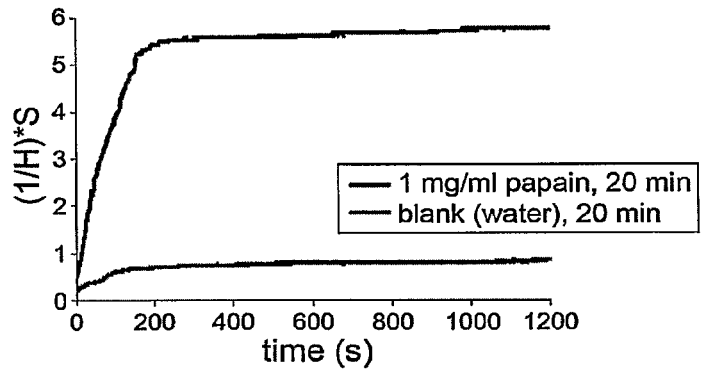
Figure 7C:
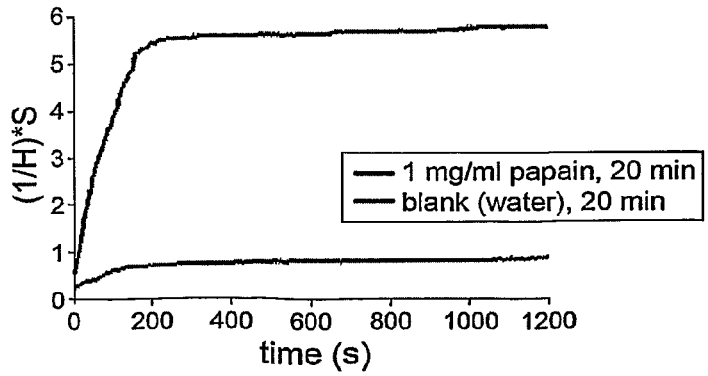

FIG. 7 includes three panels, identified as panels FIG. 7A, FIG. 7B, and FIG. 7C. Panel FIG. 7A shows images of the results of using a product for detecting a protease enzyme in accordance with one embodiment of the present invention and the resultant positive chromogenic reaction (positive protease sample). Panel FIG. 7B is a graphical representation of data obtained from an electronic reader with a positive [Top Line] and negative [Bottom Line] sample in a device in the style described in FIG. 3. Panel FIG. 7C is a graphical representation of the same positive protease sample compared with the commercially available chromogenic substrate Benzoyl-arginyl-naphthylamide (BANA). The chromogenic substrate shows improved enzyme turnover and colour production compared to BANA under identical conditions.

Figure 8A:
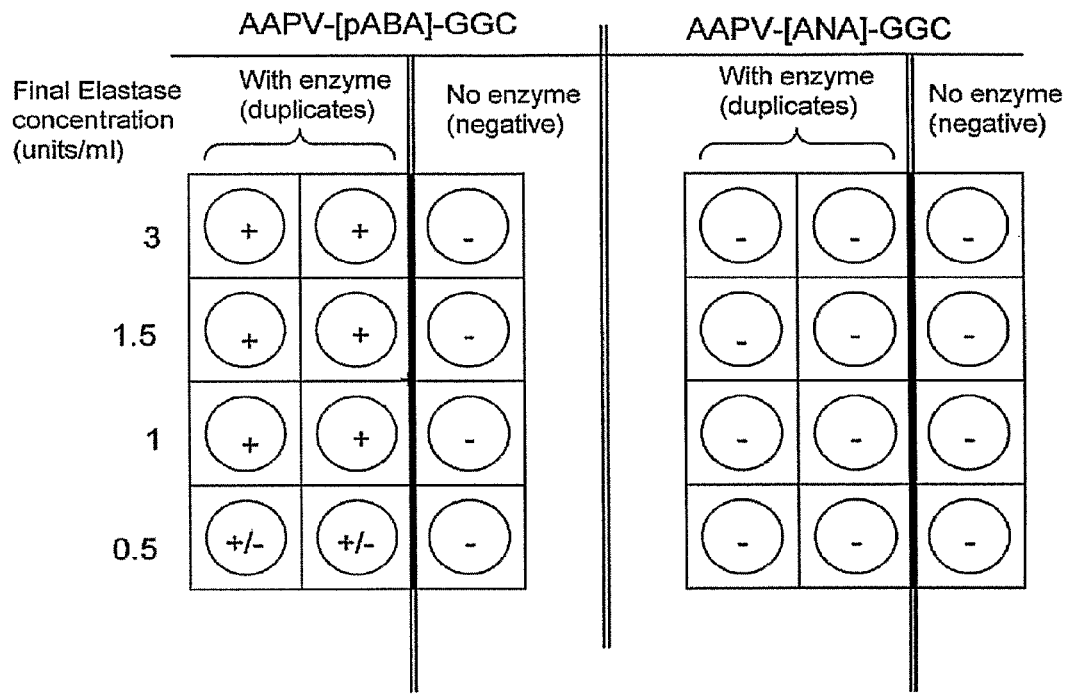
Figure 8B:
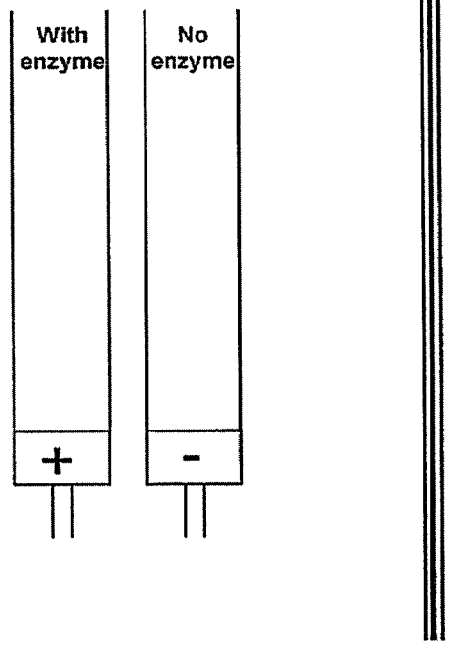
Figure 8B:
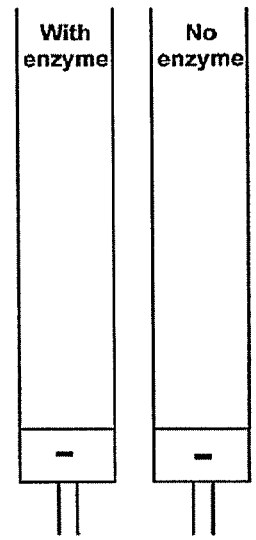
Figure 8B:
Figure 8B:

FIG. 8 includes two panels, identified as panels FIG. 8A and FIG. 8B. Panel FIG. 8A shows the results of a plate assay comparing AAPV-[pABA]-GGC (SEQ ID NO: 3) and AAPV-[ANA]-GGC (SEQ ID NO: 4) as elastase substrates. Panel FIG. 8B shows the results of a vertical flow assay comparing AAPV-[pABA]-GGC (SEQ ID NO: 3 and AAPV-[ANA]-GGC (SEQ ID NO: 4) as elastase substrates.

Figure 9:
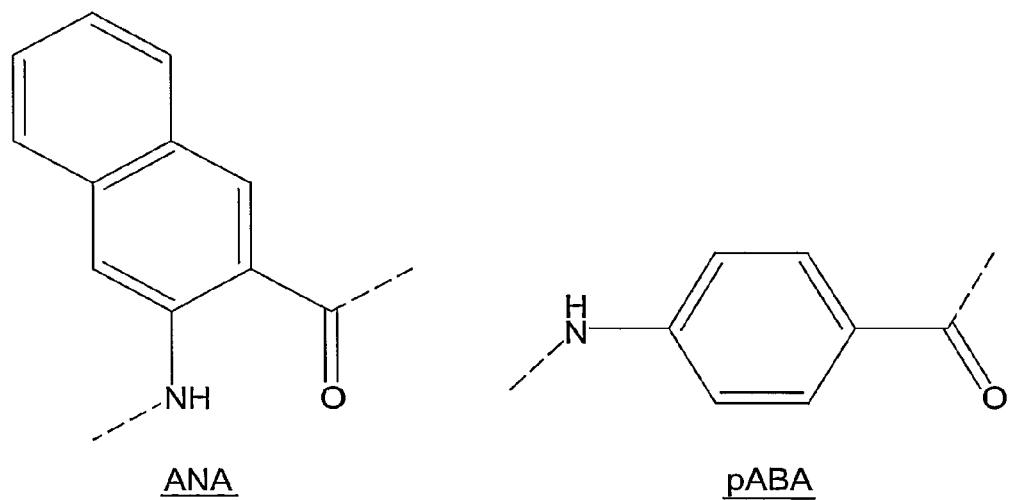

FIG. 9 shows the comparative structures of the chromogenic amino acids ANA (2-amino naphthoic acid) and pABA (para-amino benzoic acid).

Figure 10A:
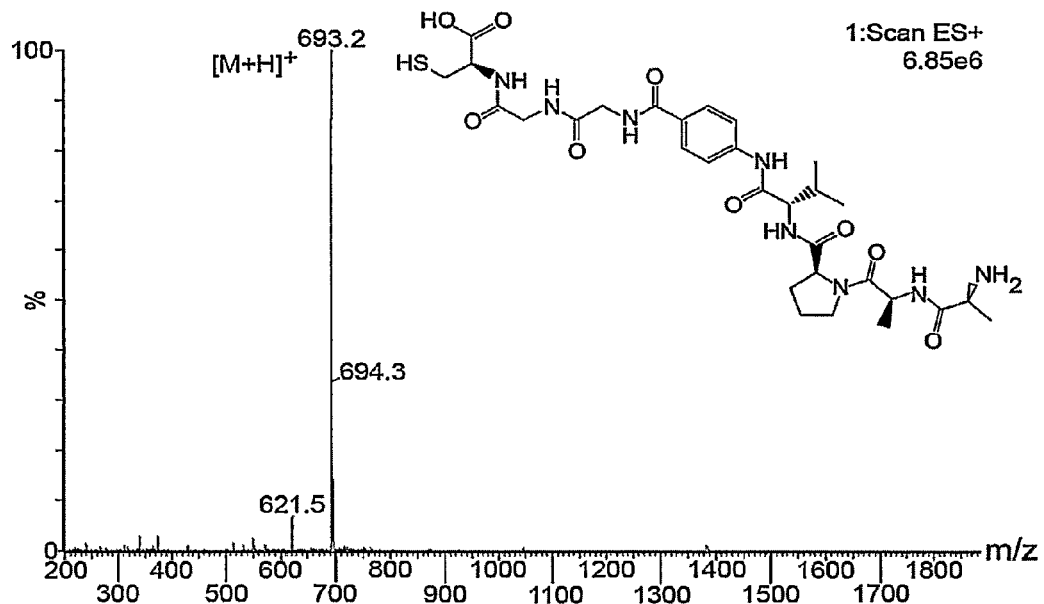
Figure 10B:
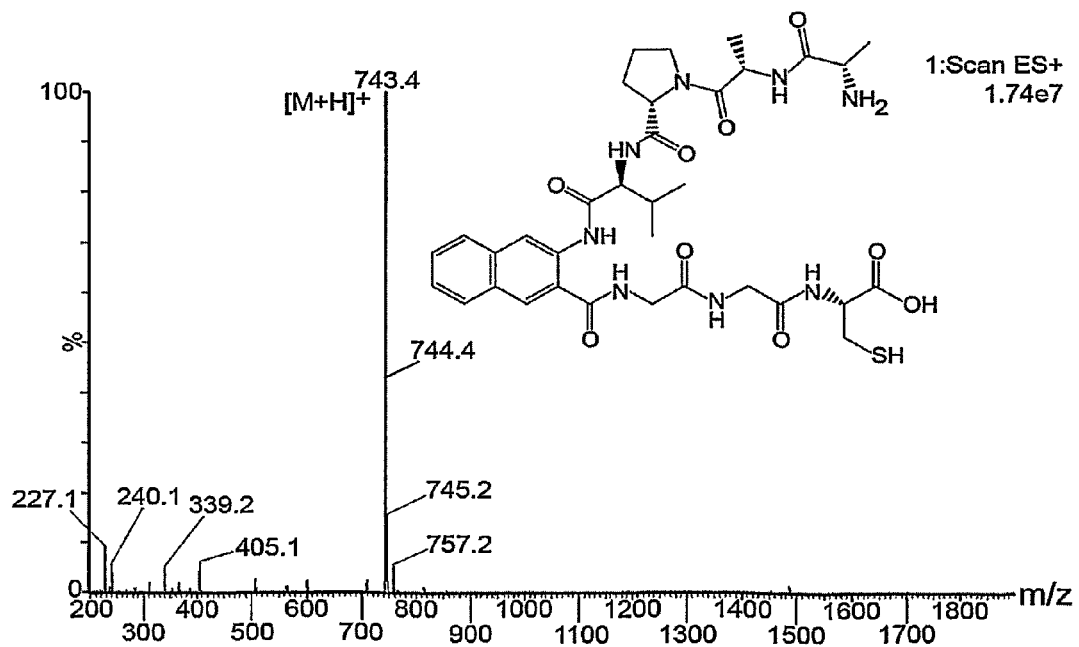

FIG. 10 includes two panels, identified as panels FIG. 10A and FIG. 10B. Panel FIG. 10A show the electrospray mass spectrum of AAPV-[pABA]-GGC (SEQ ID NO: 3); the expected mass being 692.78, and the measured mass being 692.2. Panel FIG. 10B shows the electrospray mass spectrum of AAPC-[ANA]-GGC (SEQ ID NO: 4); the expected mass being 742.84, and the measured mass being 742.4.

Figure 11:
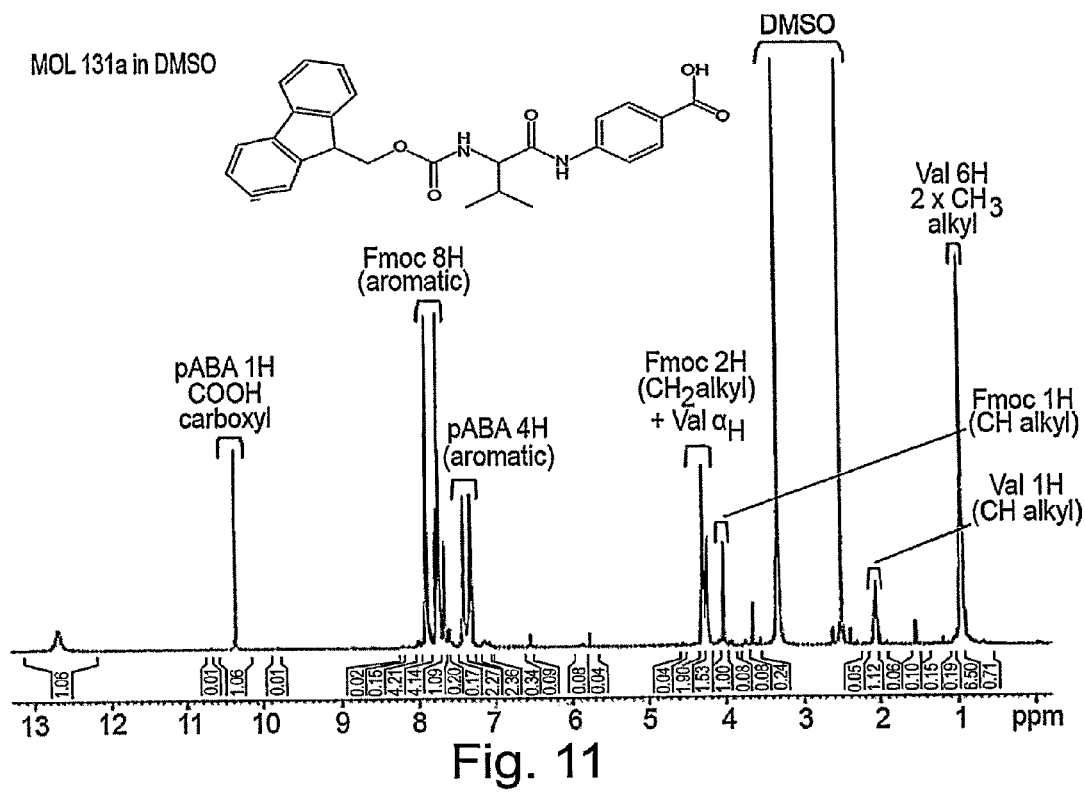

FIG. 11 shows the $^1$H NMR spectrum of Fmoc-Val-pABA-OH.

Figure 12:
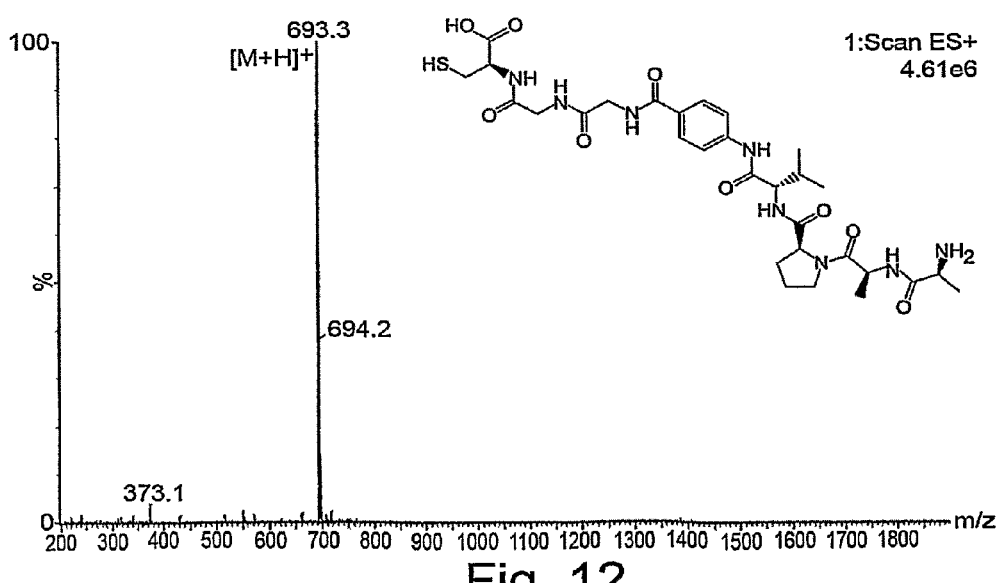

FIG. 12 shows the elecrospray mass spectrum of AAPV-[pABA]-GGC (SEQ ID NO: 3) synthesised using Fmoc-Val-pABA-GGC; the expected mass being 692.78, and the measured mass being 692.3.

In a first embodiment of the present invention there is provided a method of detecting a protease enzyme such as papain or trypsin in a sample. The method comprises providing a receptacle in which is located a cleavable polypeptide in solution. The cleavable polypeptide comprises from N-terminus to C-terminus the sequence alanine-[p-aminobenzoyl]-glycine. That is to say, the polypeptide comprises a chromogenic amino acid (p-aminobenzoic acid) flanked by two other amino acids (alanine and glycine) at its N and C termini. Polypeptides such as this, which comprise p-aminobenzoic acid, are colourless until cleaved and reacted with a second reagent. The second reagent used in this embodiment is a conjugated aldehyde Dimethyl-amino-cinnamaldehyde (DMAC).

Figure 1:
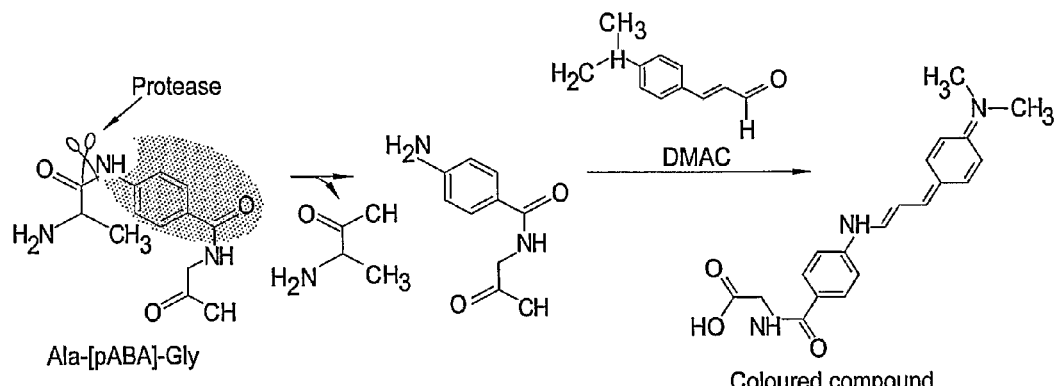
FIG. 1 shows the reaction of a polypeptide of the present invention with a protease enzyme. The sequence Ala-[pABA]-Gly (SEQ ID NO: 1) is used as an example with pancreatic elastase for simplicity, where pABA replaces alanine amino acid.

The sample is placed within a vial and mixed with the polypeptide for a sufficient length of time for the target enzyme to cleave the peptide substrate, typically less than 10 minutes. In this example, the protease cleaves the polypeptide sequence rapidly in less than 3 minutes due to the selected amino acid sequence. As a result, the protease enzyme cleaves the polypeptide at the peptide bond between the —CO-moiety of the alanine residue and the —NH— moiety of the p-aminobenzoic acid residue, as is shown in FIG. 1. This cleavage leads to the release of two molecules; a first molecule which is the free alanine residue and a second molecule which comprises the p-aminobenzoic acid residue coupled to the glycine residue. The second molecule is a chromogenic intermediate.

In the next step of the method, the DMAC is added to the vial and mixed. As is shown in FIG. 1, DMAC reacts with the chromogenic intermediate to form a coloured adduct under acidic conditions. More specifically, in a positive protease sample, the newly created chromogenic intermediate reacts with DMAC to produce a red colour. In contrast, in a negative protease sample, the substrate remains intact masking the pABA moiety rendering it un-reactive to the incoming DMAC. The DMAC molecule itself is a yellow coloured compound under mildly acidic conditions and produces a yellow colour in the absence of exposed pABA.

Therefore, the method of this embodiment of the invention gives rise to a production of colour in response to the presence (red) or absence (yellow) of a protease enzyme in a sample.

In accordance with the embodiment exemplified in FIG. 1, the peptide bond on the amino side of the chromogenic amino acid within the polypeptide is hydrolysed by the target protease, so exposing the amine group of the chromogenic amino acid. In this embodiment, the conjugated aldehyde is DMAC but alternative aldehydes can be used in other embodiments such as substituted benzaldehydes and cinnamaldehydes e.g. Dimethyl-amino-Benzaldehyde (DMAB).

The synthesis of a polypeptide in accordance with embodiments of the invention will now be described. The chromogenic polypeptides are synthesised by conventional Fmoc chemistry on a solid phase familiar to those skilled in the art. In some embodiments, each amino acid coupling is achieved by using the activated ester of the incoming amino acid. In other embodiments, an acid chloride is used to couple the incoming amino acid to the chromogenic residue. Efficiency improvements can be gained by synthesising a building block comprising the P1 amino acid and chromogen (P1') prior to the peptide synthesis, and introduced as the entire building block as a single moiety. An example of such a building block is Fmoc-alanyl-para-aminobenzoic acid which may be added to a nascent polypeptide in the same way as an amino acid. The length of the polypeptide typically ranges from 2 to 100 residues. It is easy to synthesise chromogenic polypeptides of various lengths using this method and automation of this method of manufacture is readily available. This is advantageous with regard to scaling-up production for commercial use. Also, the chromogenic polypeptides of the present invention have no known carcinogenic properties, therefore this would not be a safety issue in large scale manufacture.

Figure 2:
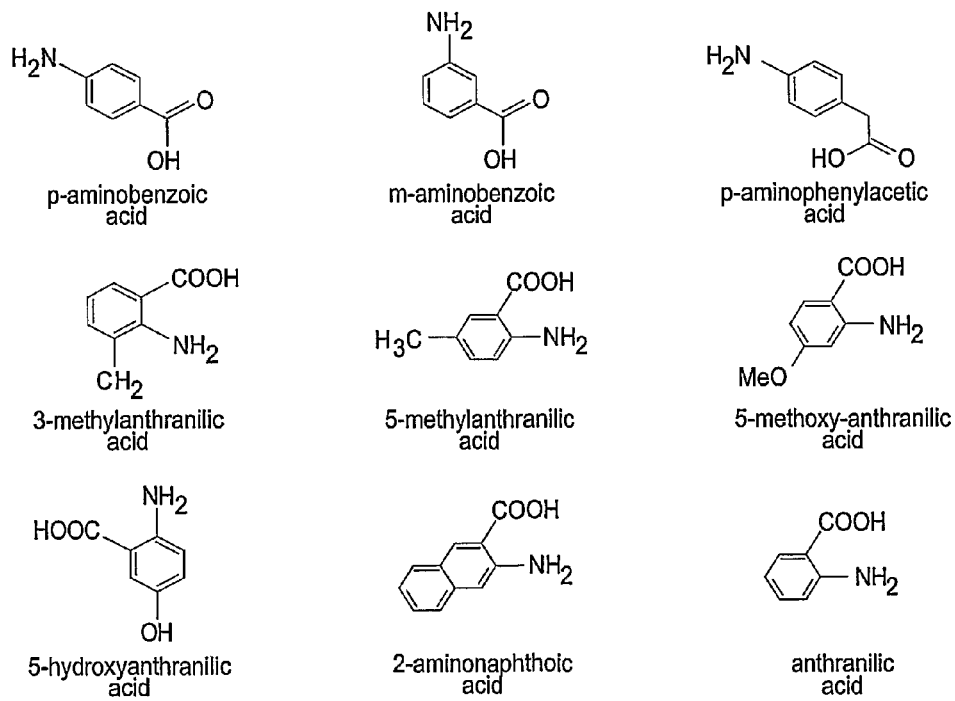
FIG. 2 shows a selection of chromogenic amino acids for use in embodiments of the present invention.

In the first embodiment, the polypeptide comprises the chromogenic amino acid p-aminobenzoic acid. However, in alternative embodiments a different chromogenic amino acid is used such as one shown in FIG. 2. These chromogenic amino acids contain an aromatic moiety (e.g. phenyl or naphthyl) or another heterocyclic analogue and the aromatic ring moiety is proximal to the amino group of the chromogenic amino acid (i.e. it is an aniline). Nevertheless, it is to be understood that in further embodiments of the present invention, chromogenic acids are provided which do not comprise an aromatic ring moiety. What is important is that the amine group of the chromogenic amino acid has a pKa significantly lower (e.g. less than 5) than any other amino acid (amino terminus or side chain) present in the polypeptide. In this way, under conditions of low pH, the chromogenic amine is at least partially deprotonated whereas the other amines in the structures present are virtually completely protonated. This permits the reaction with the conjugated aldehyde to occur predominantly with the chromogenic amino acid. It is also necessary, of course, for the chromogenic acid to be such that steric hindrance does not prevent interaction with the conjugated aldehyde.

Ideally, the chromogenic amino acid used in the polypeptide is isosterically matched to a natural amino acid so as to mimic the structure of the substrate of the target protease as closely as possible. Therefore, chromogenic polypeptides with target regions that are specific for individual target proteases are synthesised. The chromogenic amino acid may be positioned anywhere within the polypeptide peptide, with the proviso that it is not located at the C-terminus of the amino acid.

Figure 3:
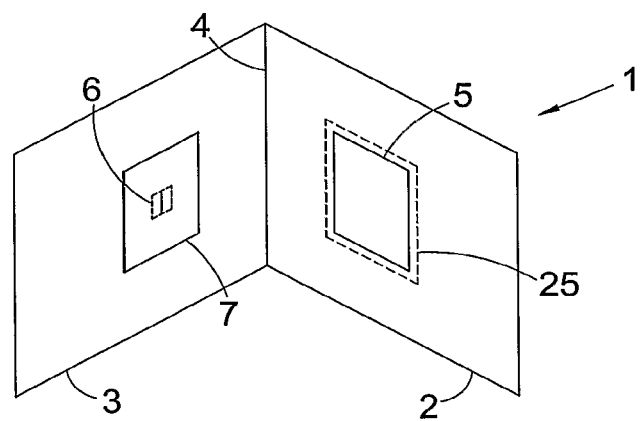
FIG. 3 shows a perspective view of a product for detecting a protease enzyme in accordance with one embodiment of the present invention.

The polypeptides of the present invention are, in some embodiments, incorporated into a product for detecting a protease enzyme in a sample which takes the form of a booklet. A suitable such booklet is disclosed in PCT application No. PCT/GB2007/000643 which is incorporated herein by reference. Referring to FIG. 3 a booklet 1 in accordance with this embodiment will now be described. The booklet comprises first and second sheets 2, 3 of planar substrate such as cardboard, connected by a hinge 4. In the centre of the first sheet there is provided a thin reaction film 25 on top of an absorbent pad 5. The reaction film 25 is impregnated with the chromogenic polypeptide and can be made from PVA. On the centre of the second sheet 3 there is provided an aperture 6 which is aligned with the reaction film 25 and the absorbent pad 5. The aperture 6 is covered by a visualisation film 7, such that the visualisation film 7 lies between the aperture 6 and the reaction film 25 when the first and second sheets 2, 3 are pressed against each other. The visualisation film 7 is impregnated with DMAC and HCl. Optionally, the reaction film 25 and the absorbent pad 5 are covered with a removable film (not shown) prior to use so that the reaction film 25 and the absorbent pad 5 are kept sealed from the environment.

In use, any removable film covering the reaction film 25 and the absorbent pad 5 is peeled away and a sample suspected of containing a protease enzyme is deposited on the reaction film 25 and soaks into the absorbent pad 5. If a protease is present in the sample then the protease cleaves the chromogenic polypeptide to release the chromogenic intermediate as has been described in the first embodiment. The first and second sheets 2, 3 of the booklet 1 are then pressed together so that the components on the reaction film 25 are brought into contact with the visualisation film 7 and, more specifically, with DMAC.

Thus some of the chromogenic intermediate passes from the reaction film 25 and the absorbent pad 5 on to the visualisation film 7 where it reacts with DMAC to form the coloured adduct. As described above, the coloured adduct is red in colour and this is visible through the aperture 6 to a user of the booklet 1.

Alternatively, if the sample does not contain a protease enzyme which is capable of cleaving the chromogenic polypeptide, then the chromogenic intermediate is not formed and the chromogenic polypeptide remains yellow in colour. Thus the visualisation film either retains its colour or is coloured yellow.

In a variant of this embodiment, a membrane is provided, which covers the visualisation film and which does not allow material above a certain threshold size to pass through it. The threshold is selected so that any material in the sample which naturally has a colour is too big to pass through the membrane but that the chromogenic intermediate is small enough to pass through the membrane and can therefore come into contact with the visualisation film and, more specifically, DMAC thereon.

Figure 4:
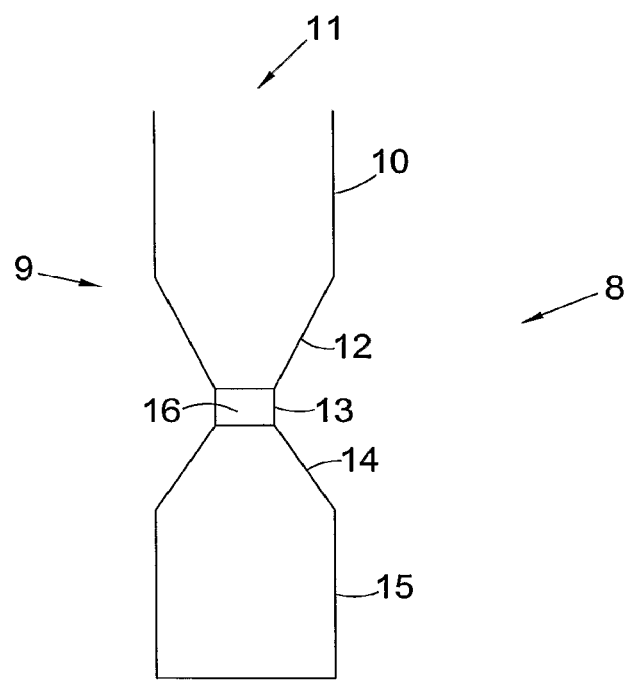
FIG. 4 shows a cross sectional view of a product for detecting a protease enzyme in accordance with another embodiment of the present invention.

Referring, now, to FIG. 4 a further embodiment of the present invention will be described. In this embodiment, the polypeptide of the present invention is incorporated into a product for detecting a protease enzyme which takes the form of a vertical flow biochemical assay. A detection device 8 comprises a receptacle 9 having an upper section 10 with an opening 11 at its top end and, at its bottom, a funnel 12, connected to a neck 13. The neck 13 is made from a transparent material such as perspex or glass and leads to an inverted funnel 14 which, in turn, is at the top of a lower section 15. The neck 13 encloses a matrix 16 in which are immobilised a plurality of chromogenic polypeptides of the present invention. For example, in some embodiments, the matrix 16 comprises a plurality of particles onto which the chromogenic polypeptide is covalently bonded at or near its C-terminus with an amide bond or via a thiol interaction (forming a thio ether). In this context, "near" means within 10 or 20 amino acid residues of the C-terminus.

In use, a sample suspected of containing a protease enzyme is added by the open end 11 of the upper section 10 of the receptacle 9 so that it flows into the funnel 12 and is slowly released into the matrix 16. The sample passes through the matrix 16 at a constant rate by gravity and capillary action. The protease in the sample cleaves the chromogenic polypeptide in the matrix 16 at the peptide bond between the —NH— moiety of the chromogenic amino acid and the —CO— moiety of the amino acid immediately adjacent in the N-terminal direction. Thus the N-terminal fragment of the chromogenic polypeptide is released and the chromogenic intermediate remains immobilised in the matrix 16. Optionally, the sample is washed through with a buffer so as to ensure that all N-terminal fragments are washed through the matrix 16 and into the lower portion 15 in the receptacle 9.

Subsequently, a container (not shown) holding a buffer including DMAC is located above the open end 11 of the upper portion 10 of the receptacle 9 and is punctured at its lower end so as to release the buffer into the funnel 12 of the receptacle 9. The buffer containing DMAC flows through the matrix 16 and, where it comes into contact with the chromogenic intermediate, reacts with it to form the coloured adduct. Any excess DMAC flows through the substrate 16 and into the lower portion 15 of the receptacle 9. As has previously been explained, the coloured adduct is red in colour and thus the presence of a protease in a sample results in the matrix 16 turning red. This is visible through the neck 13.

Alternatively, if the sample does not contain a protease enzyme which is capable of cleaving the chromogenic peptide at the target sequence, the chromogenic peptide in the matrix 16 remains uncleaved and thus there is no chromogenic intermediate for the DMAC to react with. DMAC is yellow in colour and some remains in the matrix 16 by non-specific adhesion. Thus in response to a protease negative sample, the matrix 16 turns yellow in colour.

It has been observed that, during the synthesis of chromogenic polypeptides, the amide coupling reaction of a natural amino acid to the —NH$_2$— moiety of a chromogenic amino acid is a relatively inefficient part of the synthesis. Consequently, the synthesis reaction often produces a proportion of incomplete polypeptides in which no amino acids are present attached to the N-terminus of the chromogenic amino acid. If the proportion of such incomplete polypeptides is significant then this can lead to false positive results because the incomplete polypeptides have the same structure as the chromogenic intermediate and are attached to the matrix 16 along with the complete polypeptides. Therefore, the incomplete polypeptides will react with DMAC and produce a colour change even in the absence of a protease in the sample. Accordingly, in some alternative embodiments, the chromogenic polypeptides are immobilised (e.g. covalently bonded) to the matrix 16 via their N-termini. In this way, any incomplete polypeptides are not bound to the matrix because they lack the N-terminal amino acid used for attachment to the matrix 16. In such embodiments, the chromogenic intermediate is released from the matrix 16 when a sample is applied that contains an active protease and an absorbent sump (e.g. a cotton wool bung) is provided beneath the matrix 16 in order to capture the released chromogenic intermediate and display the colour change.

In further embodiments of the present invention the chromogenic polypeptide comprises first and second binding moieties at either end. An example of the synthesis of such a polypeptide is provided in Example 2. In this particular embodiment, Biotin is bound to the C-terminal end of the polypeptide and Fluorescein is bound to the N-terminal end.

Figure 5:
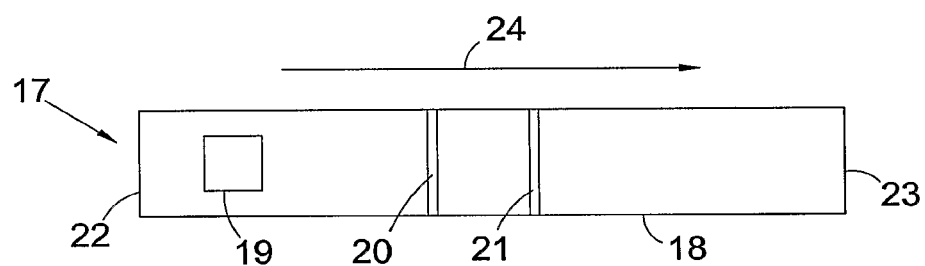
FIG. 5 shows a plan view of a product for detecting a protease enzyme in accordance with a further embodiment of the present invention.

The chromogenic polypeptide is used in a bifunctional ligand capture protease detection assay involving lateral flow. Further details of a lateral flow assay are provided in PCT Application No. PCT/GB2007/000637 and GB0716492.4 which are incorporated herein by reference. Referring to FIG. 5, a lateral flow device 17 comprises a nitrocellulose strip 18 having an upstream end 22 and a downstream end 23. A sample receiving zone 19 made from an absorbent material is located adjacent the upstream end 22. Further towards the downstream end 23 there is a first visualisation zone 20. Still further towards the downstream end 23 is a second visualisation zone 21. The first visualisation zone 20 comprises a plurality of polypeptide binding molecules immobilised on the surface of the strip 18. Each of the polypeptide binding molecules is capable of binding the chromogenic polypeptide by its C-terminal end. In this particular embodiment, therefore, the first polypeptide binding molecule is streptavidin which can bind the biotin on the C-terminus of the polypeptide. The second visualisation zone 21 comprises a plurality of anti-mouse antibodies, immobilised on the surface of the strip 18.

In use, a sample suspected of containing a protease enzyme is mixed with a plurality of chromogenic polypeptides as described above. The protease enzymes are allowed to cleave the polypeptide to release a chromogenic intermediate corresponding to the C-terminal end of the polypeptide and a fragment corresponding to the N-terminal end of the polypeptide. To the mixture is then added mouse anti-FITC-gold antibodies which bind the fluorescein group attached to the N-terminal fragment. The sample mixture is placed on the sample receiving zone 19. The sample mixture is then adsorbed along the length of the nitrocellulose strip 18 due to capillary action towards the downstream end 23 in the direction of the arrow 24. Thus it passes through the first visualisation zone 20, then through the second visualisation zone 21.

As the sample mixture passes the first visualisation zone 20 the biotin tag binds to the streptavidin and the chromogenic intermediate is immobilised on the first visualisation zone 20. The chromogenic intermediate remains bound to the first visualisation zone and the N-terminal fragment is adsorbed further along the nitrocellulose strip 20 to the second visualisation zone 21. The anti-mouse antibodies bind to the mouse anti-FITC-Gold antibody, so immobilising the N-terminal fragment at the second visualisation zone 21

Subsequently, DMAC is added to the sample receiving zone 19 and it is adsorbed along the strip 18 in the direction of the arrow 24. When the DMAC reaches the first visualisation zone it reacts with the immobilised chromogenic intermediate and a red coloured adduct is formed. Additionally, the gold particles bound to the anti-FITC antibody can be observed as they form a visible line at the second detection zone 21 on the nitrocellulose strip 18.

Alternatively, if there is no protease enzyme in the sample then the entire polypeptide is immobilised at the first detection zone as it is adsorbed along the nitrocellulose strip 18. Subsequently, when DMAC is added to the sample receiving zone 19, it is adsorbed along the nitrocellulose strip 18 but, since the chromogenic amino acid is not exposed on the polypeptide, the DMAC passes through the first detection zone without reacting. Thus there is no colour formed at the first detection zone 20 (except for any residual DMAC, which is yellow in colour) and, moreover, the gold particles are concentrated at the first detection zone 20. Therefore, the absence of a functional protease enzyme from the sample is indicated by the presence of a visible line formed by the gold particles, instead of a red colour, at the first detection zone 20 and the absence of a visible line from the second detection zone 21.

Therefore, this embodiment enables the detection of two waves of reactivity, one using DMAC and another using gold particle detection.

EXAMPLES

Example 1

Synthesis of Val-Arg-[pABA]-Gly (SEQ ID NO: 2)

With reference to FIG. 6, the synthesis of Val-Arg-[pABA]-Gly (SEQ ID NO: 2) will now be described.

Peptide synthesis was carried out on solid phase (Wang Resin Merck Biosciences) using Fmoc-chemistry (Fmoc solid phase synthesis—a practical approach. 2000 Chan, W C and White, P D Oxford University Press). In a typical synthesis 50 mg of resin (loading 0.91 mmol/g) was swollen in Dimethyl Formamide (DMF) (2 ml) for 1 hour in a 20 μm filtration column (Kinesis). The resin was further rinsed with DMF (2×2 ml) and drained under vacuum to dryness. The first amino acid coupling was carried out using 0.23 mmol PYBOP (benzotriazole-1-yl-oxy-tris-pyrrolidino-phosphonium hexafluorophosphate) and 0.23 mmol HOBT (hydroxybenzotriazole) and 0.23 mmol of protected glycine residue dissolved in 2 ml of dry DMF. 0.46 mmol DIPEA (diisopropylethylamine) was added to the solution which was then dispensed into the resin. The resin slurry was stirred at room temperature for 90 minutes, before drainage under vacuum and rinsing with DMF (2×2 ml). A repeat reaction was carried out to make sure total coverage of the resin reactive sites. After rinsing with DMF (3×2 ml), (Dichloromethane) DCM (3×2 ml) and one further wash with DMF (2 ml), the resin was Fmoc-deprotected by adding a solution of 20% piperidine in the DMF (5 ml) and stirring for 5 min. The resin was then rinsed with DMF (2×2 ml) and the reaction repeated once more. The resin was rinsed thoroughly in DMF (3×2 ml), DCM (3×2 ml) and then finally DMF (2 ml). This reaction was then repeated for the remaining amino acid residues. For the addition of the amino acid following the chromogenic moiety, the acid chloride was prepared prior to coupling as follows. Triphosgene (0.077 mmol) and the Fmoc protected amino acid (0.23 mmol) were dissolved in 1 ml of tetrahydrofuran (THF). 0.76 mmol Collidine was added dropwise to the solution to create a white suspension. This was then added to the resin and mixed for 1 hour at room temperature. The reaction mixture was drained and rinsed with THF (2×2 ml) and DCM (3×2 ml). The reaction was repeated to ensure completeness, and the resin was then drained and rinsed thoroughly with THF (2×2 ml), DCM (3×2 ml) and then DMF (2 ml). Deprotection was facilitated as described above.

Cleavage from the resin and deprotection of side chains was carried out by the addition of TFA:water:triethylsilane (TES) (95%:2.5%:2.5%). The slurry was stirred vigorously for 90 min. To complete the synthesis the crude peptide mixture was removed from the resin slurry with further washes of 0.1% TFA water (2×5 ml). The mixture was then evaporated to dryness and washed with dry ether (2×10 ml) by swilling the solvent carefully over the peptide residue and then decanting. The residue was air dried for an hour, before being dissolved in the minimum amount of water (3-5 ml) and filtered through a 0.2 μm filter. The filtrate was injected on to a Phenomenex Jupiter proteo column for analysis and subsequent preparative HPLC. Pure fractions were combined and evaporated to dryness and then redissolved in pure water (0.5-1 ml) snap-frozen in an eppendorf tube and freeze-dried to afford a white/colourless powdery solid. Peptides were confirmed by LC-MS using positive ion electrospray mass spectrometry.

Example 2

The Detection of Papain

The chromogenic polypeptide Val-Arg-[pABA]-Gly (SEQ ID NO: 2) was used in an assay to detect the presence of papain in a sample solution. A sample comprising the protease enzyme papain was applied to the first sheet of a booklet (see FIG. 7A) in accordance with the embodiment depicted in FIG. 3. The first sheet of the booklet had previously been impregnated with the chromogenic polypeptide. After five minutes, the first and second sheets of the booklet were folded together. The second sheet of the booklet had previously been impregnated with DMAC and after ten minutes DMAC changed from yellow to red as was observable through an aperture in the second sheet of the booklet. The assay was also repeated, as a control, with water replacing the sample and the results of the colour change are shown in the graph in FIG. 7B.

The protease assay was also repeated under identical conditions using BANA rather than the chromogenic polypeptide. The rate of colour change detected during the assays were compared and the results are displayed graphically in FIG. 7C. Val-Arg-[pABA]-Gly (SEQ ID NO: 2) was shown to elicit a faster detectable colour change than BANA (benzoyl arginyl naphthylamide), which is advantageous for an in situ detection device.

Example 3A

The Determination of a Suitable Chromogenic Substrate for Detecting the Presence of Elastase Two peptides, AAPV-[pABA]-GGC (SEQ ID NO: 3) and AAPV-[ANA]-GGC (SEQ ID NO: 4), were synthesised, wherein pABA is para-amino benzoic acid and ANA is 2-amino naphthoic acid. Both peptides were tested for their suitability as a substrate for the Neutrophil Elastase enzyme. The electrospray mass spectrums of AAPV-[pABA]-GGC (SEQ ID NO: 3) and AAPV-[ANA]-GGC (SEQ ID NO: 4) are shown in FIGS. 10A and 10B respectively.

Varying concentrations of Elastase (5 µl of 18, 9, 6 and 3 units/ml dilutions) were added to 0.5 mg/ml peptide (5 µl) in separate plate wells. The mixtures were diluted with 20 µl of Buffer (50 mM phosphate, 5 mM EDTA; pH 7.4) and incubated at 37° C. for 30 minutes. 15 µl of working DMAC solution (0.3 mg/ml DMAC, 50 mM HCl) was added to each plate well and mixed thoroughly to visualize.

The results of this experiment are shown in FIG. 8A.

The assays using AAPV-[PABA]-GGC (SEQ ID NO: 3) when the final concentration of elastase in the wells were 3, 1.5 or 1 units/ml gave a positive result (i.e. the wells turned a red/orange colour (Pantone™ 136U)) for elastase activity. This colour change was indicative of the presence of elastase. The wells with 0.5 units/ml elastase gave a weak positive result when mixed with AAPV-[pABA]-GGC (SEQ ID NO: 3) (Pantone™ 108U). The control wells gave a negative result.

In contrast, none of the wells with AAPV-[ANA]-GGC (SEQ ID NO: 4) significantly changed colour, they remained yellow (Pantone™ 394U). Therefore, elastase activity was not detected despite the presence of elastase in the wells.

Example 3B

Another assay format was used to test for the activity of the enzyme Neutrophil Elastase in the presence of the two peptides, AAPV-[pABA]-GGC (SEQ ID NO: 3) and AAPV-[ANA]-GGC (SEQ ID NO: 4). The C-terminal cysteine group of the peptides was used as a means of conjugation to a solid surface. Sintered polyethylene frits functionalised with iodoacetyl groups were rinsed in 50 mM sodium phosphate, 5 mM EDTA, pH 7.4 for 10 minutes. The frits were then transferred to a solution of 0.5 mg/ml peptide (in PBS) for sensitisation for 30 minutes. The frits were then rinsed once more in phosphate EDTA buffer for 10 minutes. The frits were loaded into empty columns and 200 µl of elastase was added with an approximate flow contact time of 30 seconds. To develop the assay, 100 µl of working DMAC solution (0.3 mg/ml DMAC, 50 mM HCl) was passed through the column.

The results of this assay are shown in FIG. 8B. The assay column which contained both AAPV-[pABA]-GGC (SEQ ID NO: 3) and the elastase enzyme gave a positive result (Pantone™ reference 1505 U*), and the column with AAPV-[pABA]-GGC (SEQ ID NO: 3), but no elastase gave a negative result (Pantone™ reference 3945 U*). The columns containing AAPV-[ANA]-GGC (SEQ ID NO: 4), one having the elastase enzyme present and the other not, both gave negative results (Pantone™ reference 3945 U*).

Conclusion of Examples 3A and 3B

A clear difference is observed between the two peptides in terms of the elastase activity that is detected in their presence. Elastase substrates preferably have serine, threonine (both have hydrophilic side chains) or glycine in the P1' position (Source: MEROPS database). Therefore, it is unlikely that a bulky chromogenic amino acid with a large hydrophobic surface would be a suitable steric match for these preferred amino acids. The naphthoic acid (ANA) is bulkier and more hydrophobic than para-amino benzoic acid (pABA) and thus AAPV-[ANA]-GGC (SEQ ID NO: 4) is a poor elastase substrate. The structures of both these molecules are shown in FIG. 9. The pABA chromogenic amino acid is a much better steric match for serine and threonine and therefore AAPV-[pABA]-GGC (SEQ ID NO: 3) is significantly more suitable as a substrate for elastase and results in elastase activity when the substrate and enzyme are mixed. Therefore, AAPV-[pABA]-GGC (SEQ ID NO: 3) can be used in detecting the presence of elastase.

Example 4

Synthesis of AAPV-[pABA]-GGC (SEQ ID NO: 3)

A new type of building block developed to improve the synthesis of peptides containing chromogenic amino acids was made, wherein the synthesis of said building block is compatible with automated synthesis. The method used to synthesise this building block does not require the use of the BTC/collidine procedure described in Example 1. The BTC/collidine procedure is effective but requires harsh conditions and produces an insoluble precipitate, making it unsuitable for use in conjunction with automated peptide synthesis.

The new type of building block was synthesised off-line and incorporates the P1 amino acid and the P1' chromogenic amino acid. It can be conveniently incorporated into a synthesis using the standard conditions employed for all the other amino acids in the sequence. Unwanted side reactions in the difficult coupling step are avoided, leading to a fast, clean procedure.

Fmoc-Val-OH (10 mmol) and t-butyl-pABA (10 mmol) were dissolved in dry pyridine (30 ml). The solution was cooled to −15° C. in a bath of ethylene glycol/dry ice and phosphorous oxychloride (1 ml, 11 mmol) was added drop wise with vigorous stirring. After 30 mins the reaction was over by TLC. Crushed ice (100 ml) was added and the aqueous mixture was extracted with ethyl acetate (3×50 ml). This organic extract was then washed with saturated NaHCO$_3$ (3×50 ml) and brine (3×50 ml). The organic extracts were then dried over anhydrous sodium sulfate. The crude mixture was evaporated to dryness, and then co-evaporated successively with toluene, ethyl acetate and methanol. The product was purified on silica gel eluting with 19:1 Dichloromethane/methanol. Purified t-Bu ester was deprotected with 1:1 TFA in dichloromethane for 1 hour and evaporated to afford a pale yellow solid. This compound was used directly in the synthesis of AAPV-[pABA]-GGC (SEQ ID NO: 3) replacing the individual pABA and valine coupling steps and successfully produced the expected peptide. The crude purity by HPLC was typically 70%, as opposed to 35% observed with the original procedure. The $^1$H NMR Spectrum of Fmoc-Val-pABA-OH is shown in FIG. 11, and the Electrospray mass spectrum of AAPV-[pABA]-GGC (SEQ ID NO: 3) synthesised using Fmoc-Val-pABA-OH is shown in FIG. 12.

The invention claimed is:

1. A method of detection of a protease enzyme in a sample, comprising the steps of:
   (i) exposing the sample to a polypeptide comprising a chromogenic amino acid, wherein the chromogenic amino acid isosterically matches a natural amino acid and is flanked by at least one amino acid to the N terminus and at least three amino acids to the C-terminus thereof, the amine group of the chromogenic amino acid has a pKa of less than 5 and the chromogenic amino acid is capable of reacting with a conjugated aldehyde, and wherein the polypeptide comprises a target sequence for a target protease which is capable of cleaving the peptide bond comprising the amino group of the chromogenic amino acid;
   and allowing the protease to cleave the polypeptide and create a fragment displaying the chromogenic amino acid to the N-terminus of the fragment;
   (ii) reacting a conjugated aldehyde with the fragment comprising the chromogenic amino acid to produce a colored adduct; and
   (iii) detecting the colored adduct, the presence of the colored adduct being indicative of the presence of the protease enzyme in the sample.

2. The method of claim 1, wherein the chromogenic amino acid comprises an aromatic ring moiety directly bonded to the nitrogen atom of the amino group of the chromogenic amino acid, wherein optionally the aromatic moiety is a phenyl or naphthyl moiety.

3. The method of claim 1, wherein the target sequence comprises the chromogenic amino acid.

4. The method of claim 1, wherein the conjugated aldehyde is a substituted benzaldehyde, a cinnamaldehyde, a trans, trans phenyl pentadienal, DMAC or DMAB.

5. The method of claim 1, wherein the polypeptide is immobilised on a solid support at or near the C or N terminus of the polypeptide, and wherein the polypeptide is optionally covalently bound to the solid support.

6. The method of claim 1, further comprising first and second binding moieties at or near the C or N terminus of the polypeptide.

7. The method of claim 1, wherein the polypeptide is between 5 and 100 amino acids long or between 5 and 40 amino acids long.

* * * * *

```
                       SEQUENCE LISTING

<160> NUMBER OF SEQ ID NOS: 5

<210> SEQ ID NO 1
<211> LENGTH: 3
<212> TYPE: PRT
<213> ORGANISM: Artificial
<220> FEATURE:
<223> OTHER INFORMATION: Chromogenic polypeptide Ala-[pABA]-Gly
<220> FEATURE:
<221> NAME/KEY: MISC_FEATURE
<222> LOCATION: (2)..(2)
<223> OTHER INFORMATION: Chromogenic amino acid

<400> SEQUENCE: 1

Ala Xaa Gly
1

<210> SEQ ID NO 2
<211> LENGTH: 4
<212> TYPE: PRT
<213> ORGANISM: Artificial
<220> FEATURE:
<223> OTHER INFORMATION: Chromogenic Polypeptide Val-Arg-[pABA]-Gly
<220> FEATURE:
<221> NAME/KEY: MISC_FEATURE
<222> LOCATION: (3)..(3)
<223> OTHER INFORMATION: Chromogenic amino acid

<400> SEQUENCE: 2

Val Arg Xaa Gly
1

<210> SEQ ID NO 3
<211> LENGTH: 8
<212> TYPE: PRT
<213> ORGANISM: Artificial
<220> FEATURE:
<223> OTHER INFORMATION: Chromogenic Polypeptide AAPV-[pABA]-GGC
<220> FEATURE:
<221> NAME/KEY: MISC_FEATURE
<222> LOCATION: (5)..(5)
<223> OTHER INFORMATION: Chromogenic amino acid

<400> SEQUENCE: 3

Ala Ala Pro Val Xaa Gly Gly Cys
1               5

<210> SEQ ID NO 4
<211> LENGTH: 8
<212> TYPE: PRT
<213> ORGANISM: Artificial
<220> FEATURE:
<223> OTHER INFORMATION: Chromogenic Polypeptide AAPV-[ANA]-GGC
<220> FEATURE:
```

```
<221> NAME/KEY: MISC_FEATURE
<222> LOCATION: (5)..(5)
<223> OTHER INFORMATION: Chromogenic amino acid

<400> SEQUENCE: 4

Ala Ala Pro Val Xaa Gly Gly Cys
1               5

<210> SEQ ID NO 5
<211> LENGTH: 5
<212> TYPE: PRT
<213> ORGANISM: Artificial
<220> FEATURE:
<223> OTHER INFORMATION: Chromogenic polypeptide Val-[pABA]-GGC
<220> FEATURE:
<221> NAME/KEY: MISC_FEATURE
<222> LOCATION: (2)..(2)
<223> OTHER INFORMATION: Chromogenic amino acid

<400> SEQUENCE: 5

Val Xaa Gly Gly Cys
1               5
```